(12) United States Patent
Collins et al.

(10) Patent No.: US 7,141,233 B2
(45) Date of Patent: *Nov. 28, 2006

(54) RADIONUCLIDE LABELING OF VITAMIN $B_{12}$ AND COENZYMES THEREOF

(75) Inventors: Douglas A. Collins, Rochester, MN (US); Henricus Petrus Hogenkamp, Roseville, MN (US)

(73) Assignees: Mayo Foundation for Medical Education and Research, Rochester, MN (US); Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/620,273

(22) Filed: Jul. 15, 2003

(65) Prior Publication Data

US 2005/0069493 A1    Mar. 31, 2005

Related U.S. Application Data

(62) Division of application No. 09/626,213, filed on Jul. 26, 2000, now Pat. No. 6,613,305, which is a division of application No. 09/354,553, filed on Jul. 15, 1999, now Pat. No. 6,096,290, which is a division of application No. 09/059,227, filed on Apr. 13, 1998, now Pat. No. 6,004,533, which is a division of application No. 08/557,955, filed on Nov. 13, 1995, now Pat. No. 5,739,313.

(51) Int. Cl.
  *A61K 49/00* (2006.01)

(52) U.S. Cl. ............... 424/9.1; 424/1.65; 424/1.11; 424/1.73; 514/52

(58) Field of Classification Search ............ 424/1.11, 424/1.73, 1.65, 1.69, 1.81, 9.1, 1.89; 534/7, 534/10–16; 536/26.4, 26.44, 26.41, 26.6; 514/25, 52; 435/6
See application file for complete search history.

(56) References Cited

U.S. PATENT DOCUMENTS

| | | |
|---|---|---|
| 3,936,440 A | 2/1976 | Nath |
| 3,981,863 A | 9/1976 | Niswender et al. |
| 4,209,614 A | 6/1980 | Bernstein et al. |
| 4,279,859 A | 7/1981 | Gutcho et al. |
| 4,283,342 A | 8/1981 | Yolles |
| 4,301,140 A | 11/1981 | Frank et al. |
| 4,465,775 A | 8/1984 | Houts |
| 5,308,606 A | 5/1994 | Wilson et al. |
| 5,405,839 A | 4/1995 | Toraya et al. |
| 5,428,023 A | 6/1995 | Russell-Jones et al. |
| 5,449,720 A | 9/1995 | Russell-Jones et al. |
| 5,548,064 A | 8/1996 | Russell-Jones et al. |
| 5,574,018 A | 11/1996 | Habberfield et al. |
| 5,589,463 A | 12/1996 | Russell-Jones et al. |
| 5,608,060 A | 3/1997 | Axworthy et al. |
| 5,739,313 A * | 4/1998 | Collins et al. ........... 536/26.44 |
| 5,807,832 A | 9/1998 | Russell-Jones et al. |
| 5,840,880 A | 11/1998 | Morgan et al. |
| 5,869,465 A | 2/1999 | Morgan et al. |
| 5,869,466 A | 2/1999 | Russell-Jones et al. |
| 5,877,165 A | 3/1999 | Miura et al. |
| 5,936,082 A | 8/1999 | Bauer |
| 6,004,533 A * | 12/1999 | Collins et al. ............ 424/1.73 |
| 6,083,926 A | 7/2000 | Morgan et al. |
| 6,096,290 A * | 8/2000 | Collins et al. ............ 424/1.65 |
| 6,150,341 A | 11/2000 | Russell-Jones et al. |
| 6,183,723 B1 | 2/2001 | Seetharam et al. |
| 6,211,355 B1 * | 4/2001 | Collins et al. ........... 536/26.41 |
| 6,262,253 B1 | 7/2001 | Russell-Jones et al. |
| 6,315,978 B1 | 11/2001 | Grissom et al. |
| 6,613,305 B1 * | 9/2003 | Collins et al. ............ 424/1.73 |
| 6,806,363 B1 * | 10/2004 | Collins et al. ............ 536/26.4 |
| 2003/0144198 A1 | 7/2003 | Collins et al. |

FOREIGN PATENT DOCUMENTS

EP    0005834    12/1979

(Continued)

OTHER PUBLICATIONS

Alvarez, J., et al., "On a new radiopharmaceutical for kidney imaging", *Int'l J. of Applied Radiation and Isotopes*, 25, 283-284 (1974).

(Continued)

*Primary Examiner*—Dameron L. Jones
(74) *Attorney, Agent, or Firm*—Fish & Richardson P.C.

(57) ABSTRACT

A compound useful for in vivo imaging of organs and tumors is provided of formula:

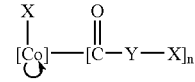

wherein

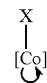

is a cobalamin,

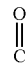

is derived from a corrin carboxylic acid group of said cobalamin, Y is a linking group and X is a chelating group, optionally comprising a detectable radionuclide or a paramagnetic metal ion, and n is 1–3.

19 Claims, 2 Drawing Sheets

FOREIGN PATENT DOCUMENTS

| | | |
|---|---|---|
| EP | 0069450 | 1/1983 |
| EP | 0165716 | 12/1985 |
| JP | 58-046027 | 9/1981 |
| WO | WO 89/01475 | 2/1989 |
| WO | WO 92/13571 | 8/1992 |
| WO | WO 94/27613 | 12/1994 |
| WO | WO 94/27641 | 12/1994 |
| WO | WO 95/27723 | 10/1995 |
| WO | WO 96/31243 | 10/1996 |
| WO | WO 97/14711 | 4/1997 |
| WO | WO 97/18231 | 5/1997 |
| WO | WO 98/08859 | 3/1998 |
| WO | WO 99/65930 | 12/1999 |
| WO | WO 00/45857 A2 | 8/2000 |
| WO | WO 00/45857 A3 | 8/2000 |
| WO | WO 00/62808 A2 | 10/2000 |
| WO | WO 00/62808 A3 | 10/2000 |
| WO | WO 01/28592 | 4/2001 |
| WO | WO 01/28595 | 4/2001 |
| WO | WO 01/30967 | 5/2001 |
| WO | WO 01/17694 | 12/2001 |
| WO | WO 01/92283 A2 | 12/2001 |
| WO | WO 01/92288 | 12/2001 |
| WO | WO 02/42318 | 5/2002 |
| WO | WO 02/55530 | 7/2002 |
| WO | WO 03/00010 A2 | 1/2003 |
| WO | WO 03/00010 A3 | 1/2003 |
| WO | WO 03/25139 A2 | 3/2003 |
| WO | WO 03/25139 A3 | 3/2003 |

OTHER PUBLICATIONS

Amagasaki, T., et al., "Expression of transcobalamin II receptors by human leukemia K562 and HL-60 cells", *Blood*, 76, 1380-1386 (Oct. 1990).

Anderson, C.J., et al., "Preparation, biodistribution and dosimetry of copper-64-labeled anti-colorectal carcinoma monoclonal antibody fragments 1 A3-F(ab')2", *J. Nuc. Med.*, 36, 850-858 (May 1985).

Anton, D.L., et al., "Carbon-13 nuclear magnetic resonance studies of the monocarboxylic acids of cyanocobalamin, assignments of the b-, d-, and 3-monocarboxylic acids", *J. Am. Chem. Soc.*, 102, 2215-2219 (Mar. 1980).

Anton, D.L., et al., "The synthesis and properties of four spin-labeled analogs of adenosylcobalamin", *J. Biol. Chem.*, 255, 4507-4510 (May 1980).

Begley, J.A., et al., "Cobalamin metabolism in cultured human chorionic villus cells", *J. Cell. Physiol.*, 156, 43-47 (1993).

Blomquist, L., et al., "Uptake of labeled vitamin B21 and 4-iodophenylanine in some tumours of mice", *Experientia*, 25, 294, 296 (1969).

Cooper, B.A., et al., "Selective uptake of specifically bound cobalt-58 vitamin B12 by human and mouse tumour cells", *Nature*, 191, 393-395 (Jul. 1961).

Cooperman, J.M., "Distribution of radioactive and nonradioactive vitamin B12 in normal and malignant tissues of an infant with neuroblastoma", *Cancer Research*, 32, 167-172 (Jan. 1972).

Cooperman, J.M., et al., "Distribution of radioactive and nonradioactive vitamin B12 in the dog", *J. Biol. Chem.*, 235, 191-194 (Jan. 1960).

Flodh, H., "Accumulation of labeled vitamin B12 in some transplanted tumours", in *Distribution and Kinetics of Labelled Vitamin B12, Acta Radiologica, Supplementum 284*, 55-60 (1968).

Flodh, et al., "Accuulation of labeled vitamin B12 in some transplanted tumours", *Int. J. Cancer*, 3, 694-499 (1968).

Kaplan, M.A., et al., "Absorptions studies of 59Fe and 58Co vitamin B12 by whole-body radiometry in the radiation therapy of collum carcinoma", *Radiobiol. Radiother.*, 24, Abstract 745 (1983).

Kikugawa, K., et al., "Direct halogenation of sugar moiety of nucleosides", *Tetrahedron Letters*, 2, 87-97 (1971).

Kollmer, W.E., et al., "On a new radiopharmaceutical for kidney imaging", *Int. J. Applied Radiation and Isotopes*, 25(6), 283-285 (1974).

Lindemans, J., et al., "Uptake of transcobalamin II-bound cobalamin by HL-60 cells: effect of differentiation induction", *Experimental Cell Research*, 184, 449-460 (1989).

Ponto, J.A., "II. Schilling Test", in *Pharmaceutical in Medical Imaging*, D.P. Swanson, et al., (eds.), MacMillan Publishing Co., Inc., New York, pp. 621-628 (1990).

Smeltzer, et al., Synthesis and characterization of fluorescent cobalamin (cobalafluor) derivatives for imaging, *Organic Letters*, 3(6), 799-801 (2001).

Vares, Y.V., et al., "Kinetic of 57 Co-cyanocobalamin distribution in organs and tissues of mice with transplanted tumours", *Eksp. Onkol*, 8, Abstract, 33-36 (1986).

Wilbur, et al., "Biotin Reagents for Antibody Pretargeting. 4. Selection of Biotin Conjugates for in Vivo Application Based on Their Dissociation Rate from Avidin and Streptavidin." *Bioconjugate Chem.*, 11(4), 569-583 (Jun. 29, 2000).

Wilbur, et al., "Evaluation of Biotin-Dye Conjugates for Use in an HPLC Assay to Assess Relative Binding of Biotin Derivatives with Avidin and Streptavidin." *Bioconjugate Chem.*, 11(4), 584-598 (Jun. 29, 2000).

Woolley, K.E., et al., "Uptake of [Co-57]-vitamin B-12 by murine tumours of many histological types", *Clin. Res.*, 41, Abstracts of National Meeting, Assoc. Amer. Physicians, p. 73A (Apr. 1993).

Wu, C., et al., Investigation of N-linked macrocycles for 111In and 90Y labeling of proteins, *Nucl. Med. Biol.*, 19, 239-244 (1992).

Allen, R.H, et al., "Isolation of Gastric Vitamin B12-binding Proteins Using Affinity Chromatography," *Journal of Biological Chemistry*, 248(10), 3660-3669 (1973).

Allen, R.H., et al., "Isolation of Vitamin $B_{12}$-binding Proteins Using Affinity Chromatography," *Journal of Biological Chemistry*, 247(23), 7695-7701 (1972).

Allen, R.H., "Human Vitamin B12 Transport Proteins," *Progress in Hematology*, vol. 9, pp. 57-84 (1975).

Collins, D., et al., "Tumor Imaging via Indium 111-Labeled DTPA-Adenosylcobalamin", *Mayo Clinic Proc.*, 74, 687-691 (1999).

Collins, D.A., et al., "Transcobalamin II imaging via radiolabeled diethylene-triaminepentaacetate cobalamin analogs", *J. Nucl. Med.*, 38(5), 717-723 (1997).

Fedosov, S.N., et al., "Binding of Cobalamin and Cobinamide to Transcobalamin from Bovine Milk," *Biochemistry*, 34, 16082-16087 (1995).

Fedosov, S.N., et al., "Transcobalamin from cow milk: isolation and physico-chemical properties," *Biochimica et Biophysica Acta*, 1292, 113-119, (1996).

Finkler, A.E., et al., "Nature of the Relationship between Vitamin B12 Binding and Cell Uptake," *Archives of Biochemistry and Biophysics*, 120, 79-85 (1967).

Hall, C.A., et al., "Cyclic Activity of the Receptors of Cobalamin Bound to Transcobalamin II," *Journal of Cellular Physiology*, 133(1), 187-191 (1987).

Hogenkamp, H., et al., "Synthesis and Characterization of nido-Carborane-Cobalamin Conjugates", *Nucl. Med. & Biol.*, 27, 89-92 (2000).

Hogenkamp, H.P.C., et al., "Diagnostic and Therapeutic Analogues of Cobalamin", *Chemistry and Biochemistry of $B_{12}$*, R. Banerjee, ed.; Wiley & Sons (1999), Part II, Section 15, pp. 385-410.

McClean, G.R., et al., "Antibodies to Transcobalamin II Block In Vitro Proliferation of Leukemic Cells," *Blood*, 89(1), 235-242 (1997).

Nexø, E., "Cobalamin Binding Proteins," in *Vitamin B12 and B12-proteins*, eds. Krantler, B.; Arigoni, D. and Golding, B.T.; Wiley & Sons, Ltd. pp. 461-475.

Rappazzo, M.E., et al., "Transport Function of Transcobalamin II," *Journal of Clinical Investigation*, 51, 1915-1918 (1972).

Soda, R., et al., "Receptor Distribution and the Endothelial Uptake of Transcobalamin II in Liver Cell Suspensions," *Blood*, 65(4), 795-802 (1985).

Uchino, H., et al., "Tissue Distribution of Coenzyme $B_{12}$ in Rats Following Intravenous Administration," *Annals of the New York Academy of Sciences*, 112(Art. 2), 844-854 (1964).

* cited by examiner

RADIONUCLIDE LABELING OF VITAMIN $B_{12}$ AND COENZYMES THEREOF

This application is a divisional of U.S. patent application Ser. No. 09/626,213, filed Jul. 26, 2000, now U.S. Pat. No. 6,613,305, which is a divisional of U.S. patent application Ser. No. 09/354,553, filed Jul. 15, 1999, now U.S. Pat. No. 6,096,290, which is a divisional of U.S. patent application Ser. No. 09/059,227, filed Apr. 13, 1998, now U.S. Pat. No. 6,004,533, which is a divisional of U.S. patent application Ser. No. 08/557,955, filed Nov. 13, 1995, now U.S. Pat. No. 5,739,313, the disclosures of which are hereby incorporated by reference.

BACKGROUND OF THE INVENTION

For several years after the isolation of vitamin $B_{12}$ as cyanocobalamin in 1948, it was assumed that cyanocobalamin and possibly hydroxocobalamin, its photolytic breakdown product, occurred in man. Since then it has been recognized that cyanocobalamin is an artifact of the isolation of vitamin $B_{12}$ and that hydroxocobalamin and the two coenzyme forms, methylcobalamin and adenosylcobalamin, are the naturally occurring forms of the vitamin.

The structure of these various forms is shown in FIG. 1, wherein X is CN, OH, $CH_3$ or adenosyl, respectively. Hereinafter, the term cobalamin will be used to refer to all of the molecule except the X group. The fundamental ring system without cobalt (Co) or side chains is called corrin and the octadehydrocorrin is called corrole. The Co-contg heptacarboxylic acid resulting from hydrolysis of all the amide groups without the CN and the nucleotide, is designated cobyrinic acid. The corresponding hexacarboxylic acid with D-1-amino-2-propanol side chain f is called cobinic acid and the hexacarboxylic acid with the α-D-ribofuranose-3-phosphate attached to the 2-position of the amino propanol is called cobamic acid. Thus, cobamide is the hexaamide of cobamic acid, cobyric acid is the hexaamide of cobyrinic acid and cobinamide is the hexaamide of cobinic acid. FIG. 1 is adapted from *The Merck Index*, Merck & Co. (11th ed. 1989), wherein X is above the plane defined by the corrin ring and nucleotide is below the plane of the ring. The corrin ring has attached six amidoalkyl ($H_2NC(O)Alk$) substituents, at the 2, 3, 7, 8, 13, and 18 positions, which can be designated a–e and g, respectively. See D. L. Anton et al., *J. Amer. Chem. Soc.*, 102, 2215 (1980). The molecule shown in FIG. 1 can be abbreviated as shown below:

wherein, e.g., X is CN, OH, $CH_3$, or adenosyl.

Methylcobalamin serves as the cytoplasmic coenzyme for $^5$N-methyltetrahydrofolate:homocysteine methyl transferase (methionine synthetase, EC 2.1.1.13), which catalyzes the formation of methionine from homocysteine. Adenosylcobalamin is the mitochondrial coenzyme for methylmalonyl CoA mutase (EC5.4.99.2) which interconverts methylmalonyl CoA and succinyl CoA.

All forms of vitamin $B_{12}$ (adenosyl-, cyano-, hydroxo-, or methylcobalamin) must be bound by the transport proteins, Intrinsic Factor and Transcobalamin II to be biologically active. Specifically, gastrointestinal absorption of vitamin $B_{12}$ relies upon the intrinsic factor-vitamin $B_{12}$ complex being bound by the intrinsic factor receptors in the terminal ileum. Likewise, intravascular transport and subsequent cellular uptake of vitamin $B_{12}$ throughout the body is dependent upon transcobalamin II and the cell membrane transcobalamin II receptors, respectively. After the transcobalamin II-vitamin $B_{12}$ complex has been internalized, the transport protein undergoes lysozymal degradation, which releases vitamin $B_{12}$ into the cytoplasm. All forms of vitamin $B_{12}$ can then be interconverted into adenosyl-, hydroxo-, or methylcobalamin depending upon cellular demand. See, for example, A. E. Finkler et al., *Arch. Biochem. Biophys.*, 120, 79 (1967); C. Hall et al., *J. Cell Physiol.*, 133, 187 (1987); M. E. Rappazzo et al., *J. Clin. Invest.*, 51, 1915 (1972) and R. Soda et al., *Blood*, 65, 795 (1985).

Cells undergoing rapid proliferation have been shown to have increased uptake of thymidine and methionine. (See, for example, M. E. van Eijkeren et al., *Acta Oncologica*, 31, 539 (1992); K. Kobota et al., *J. Nucl. Med.*, 32, 2118 (1991) and K. Higashi et al., *J. Nucl. Med.*, 34, 773 (1993)). Since methylcobalamin is directly involved with methionine synthesis and indirectly involved in the synthesis of thymidylate and DNA, it is not surprising that methylcobalamin as well as Cobalt-57-cyanocobalamin have also been shown to have increased uptake in rapidly dividing tissue (for example, see, B. A. Cooper et al., *Nature*, 191, 393 (1961); H. Flodh, *Acta Radiol. Suppl.*, 284, 55 (1968); L. Bloomquist et al., *Experientia*, 25, 294 (1969)). Additionally, upregulation in the number of transcobalamin II receptors has been demonstrated in several malignant cell lines during their accelerated thymidine incorporation and DNA synthesis (see, J. Lindemans et al., *Exp. Cell. Res.*, 184, 449 (1989); T. Amagasaki et al., *Blood*, 26, 138 (1990) and J. A. Begly et al., *J. Cell Physiol.* 156, 43 (1993).

Vitamin $B_{12}$ has several characteristics which potentially make it an attractive in vivo tumor imaging agent. Vitamin $B_{12}$ is water soluble, has no known toxicity, and in excess is excreted by glomerular filtration. In addition, the uptake of vitamin $B_{12}$ could potentially be manipulated by the administration of nitrous oxide and other pharmacological agents (D. Swanson et al., *Pharmaceuticals in Medical Imaging*, MacMillan Pub. Co., NY (1990) at pages 621–628).

Bacteria naturally insert Cobalt-59 into the corrin ring of vitamin $B_{12}$. Commercially this has been exploited by the fermentative production of Co-56, Co-57, Co-58, and Co-60 radiolabeled vitamin $B_{12}$. For example, see Chaiet et al., *Science*, 111, 601 (1950). Unfortunately Cobalt-57, with a half life of 270.9 days, makes Co-57-cyanocobalamin unsuitable for clinical tumor imaging. Other metal ions (cobalt, copper and zinc) have been chemically inserted into naturally occurring descobaltocorrinoids produced by *Chromatium* and *Streptomyces olivaceous*. Attempts to chemically insert other metal ions in these cobalt free corrinoid rings has been unsuccessful. The placement of metals (cobalt, nickel, palladium, platinum, rhodium, zinc, and lithium) into a synthetic corrin ring has not presented any major difficulties. However, their instability and cost to produce makes them impractical for biological assays. Although Co-59 is a weakly paramagnetic quadrapolar nuclei in the $2^+$ oxidation state, Co-59 exists in the $3^+$ oxidation state within the corrin ring of vitamin $B_{12}$ and is diamagnetic. Therefore, insertion of either a radioactive or paramagnetic metal ion other than cobalt into the corrin ring does not seem feasible at this time.

A process for preparing $^{125}$I-vitamin $B_{12}$ derivatives is described in Niswender et al. (U.S. Pat. No. 3,981,863). In this process, vitamin $B_{12}$ is first subjected to mild hydrolysis to form a mixture of monocarboxylic acids, which Houts, infra, disclosed to contain mostly the (e)-isomer. The mixture is then reacted with a p-(aminoalkyl)phenol to introduce a phenol group into the $B_{12}$ acids (via reaction with one of the free carboxylic acid groups). The mixed substituent $B_{12}$ derivatives are then iodinated in the phenol-group substituent. This U.S. patent teaches that the mixed $^{125}I$—$B_{12}$ derivatives so made are useful in the radioimmunoassay of $B_{12}$, using antibodies raised against the mixture.

T. M. Houts (U.S. Pat. No. 4,465,775) reported that the components of the radiolabelled mixture of Niswender et al. did not bind with equal affinity to IF. Houts disclosed that radioiodinated derivatives of the pure monocarboxylic (d)-isomer are useful in assays of $B_{12}$ in which IF is used. However, although Houts generally discloses that the monocarboxylic (d)-isomer can be labelled with fluorophores or enzymes and used in competitive assays for vitamin $B_{12}$ in fluids, a continuing need exists for labelled vitamin $B_{12}$ derivatives suitable for tumor and organ imaging and therapy.

SUMMARY OF THE INVENTION

The present invention provides detectable compounds of the general formula (I):

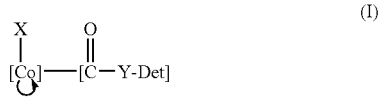

wherein the moiety

is cobalamin, X is CN, OH methyl or adenosyl,

is the residue of a monocarboxylic acid of the cobalamin, derived from a corrin propionamide group, and is preferably the essentially pure (b)-, (d)-, or (e)-monocarboxylic acid; Y is a linking group and Det is a chelating group comprising a detectable metal, such as a radionuclide or paramagnetic metal ion. Preferably, the linking group is —N(H)(CH$_2$)$_{2-6}$NH—.

For example, compounds of formula (I) derived from the (b)-monocarboxylic acid, wherein Det is the diethylenetriaminepentaacetic acid group (DTPA), were prepared comprising Tc-99n, In-111 and Gd-153. These compounds were found to be readily absorbed through the mammalian peritoneal membrane and gastrointestinal tract, to localize within the liver, kidney, pancreas, and spleen. Therefore, the present compounds can be used to evaluate hepatic, splenic, renal, pancreatic, and small bowel function in mammals such as humans and experimental animals, by administering a compound of formula (I) to the mammal and detecting its presence in the target organ, using appropriate normal control values for comparison.

Certain neoplastic tissue has been found to act as a vitamin $B_{12}$ sink, accumulating the vitamin to a greater extent than the surrounding slower dividing tissue. Therefore, the present compounds can also be used for tumor imaging and/or targeted cancer therapy, by administering a compound of formula (I) to a mammal afflicted with a tumor, so that the compound localizes in the tumor, and optionally, detecting the presence of the compound in the tumor, particularly tumors of the organs listed above.

Intermediates useful in the preparation of the compounds of formula (I) are also an aspect of the invention, including compounds wherein Det is replaced by Chel, which is an organic chelating group, or chelator, capable of chelating a radionuclide or radioisotope.

DETAILED DESCRIPTION OF THE INVENTION

Figure 1:
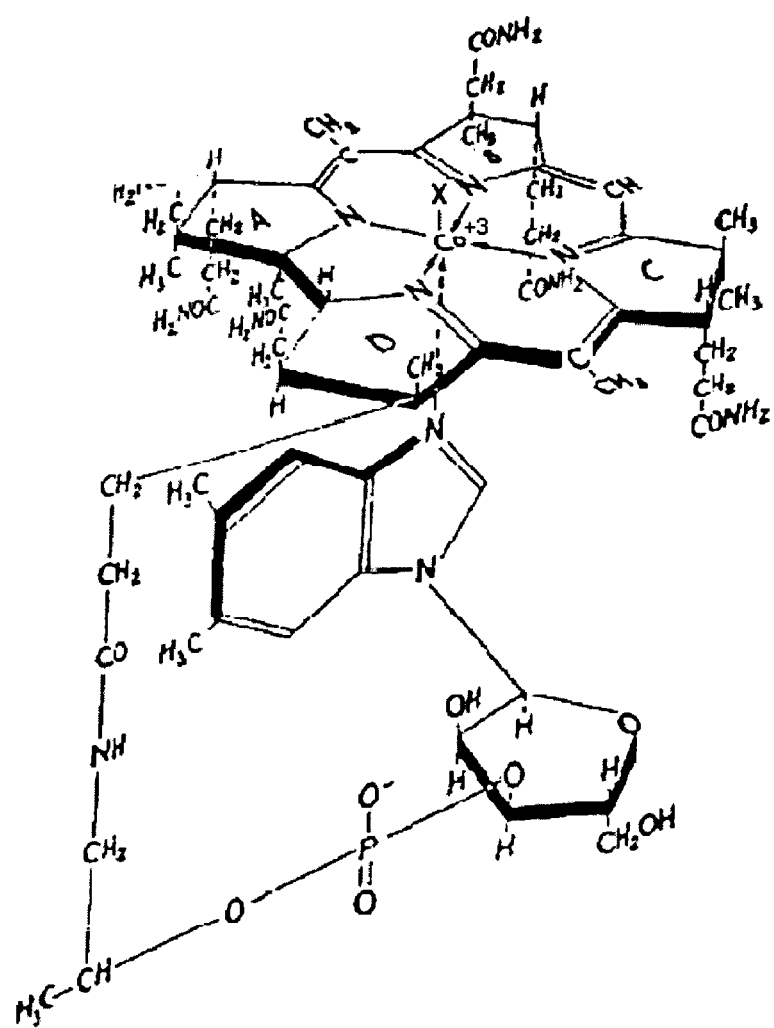
FIG. 1 depicts the structure of vitamin $B_{12}$, wherein X is CN (cyano), OH, CH$_3$ or adenosyl.

The compounds of formula I can be prepared by producing a monocarboxylic acid of X-[cobalamin], wherein X is cyano-, methyl, adenosyl, and the like. These compounds can be prepared by the mild acid hydrolysis of cyanocobalamin, which has been shown to yield a mixture of mono-, a dicarboxylic acids and one tricarboxylic acid. These carboxylic acids are derived from the propionamide side chains designated b, d and e, as discussed hereinabove, which are more susceptible to hydrolysis than the amide groups on acetamide side chains a, c, and g. The (b)-, (d)-, and (e)-monocarboxylic acids can be separated by column chromatography. See FIG. 1 herein, and FIG. 1 of D. L. Anton et al., *J. Amer. Chem. Soc.*, 102, 2215 (1980). See, also, J. B. Armitage et al., *J. Chem. Soc.* 3349 (1953); K. Bernhauer, *Biochem. Z.*, 344, 289 (1966); H. P. C. Hogenkamp et al., *Biochemistry*, 14, 3707 (1975); and L. Ellenbogen, in "Cobalamin," *Biochem. and Pathophysiol.*, B. Babior, ed., Wiley, N.Y. (1975) at chapter 5.

The X-[cobalamnin] [CO$_2$H] can be linked to the metal chelator by means of a linking group, which is preferably a divalent, or "bifunctional" organic linking group. Such linking groups comprise two reactive groups, one that is coupled to the CO$_2$H group, and the other that is coupled to the metal chelator. A variety of homobifunctional and heterobifunctional linking reagents known in the art are useful in the present invention. Preferred linkers comprise one or two amino or hydroxyl groups, such as ω-aminoalkanoic acids, e.g., ε-amino caproic acid (H$_2$N—(CH$_2$)$_5$—COOH), or alkane diamines including 1,4-diaminobutane, 1, 5-diaminopentane and 1,6-diaminohexane, and the like. Particularly preferred among the aminoalkanoic acids and similar compounds are those which are soluble in aqueous buffers.

Det is a chelating group comprising a radionuclide, such as a metallic radioisotope. Preferred among these chelating compounds "chelators" or (chel) are such polycarboxylic acids as EDTA, DTPA, DCTA, DOTA, TETA, or analogs or homologs thereof.

DTPA (diethylenetriaminepentaacetic acid) can be attached to cobalamin carboxylic acid(s) via reaction of diethylenetriaminepentaacetic dianhydride (Aldrich Chem. Co.) with a linker comprising a free amino group. This yields a Chel group that is 2-(amidomethyl)-1,1,7,7-diethylenetriaminetetraacetic acid. This chelator can be reacted with radionuclides to yield a Det moiety of the general formula

Figure 2:
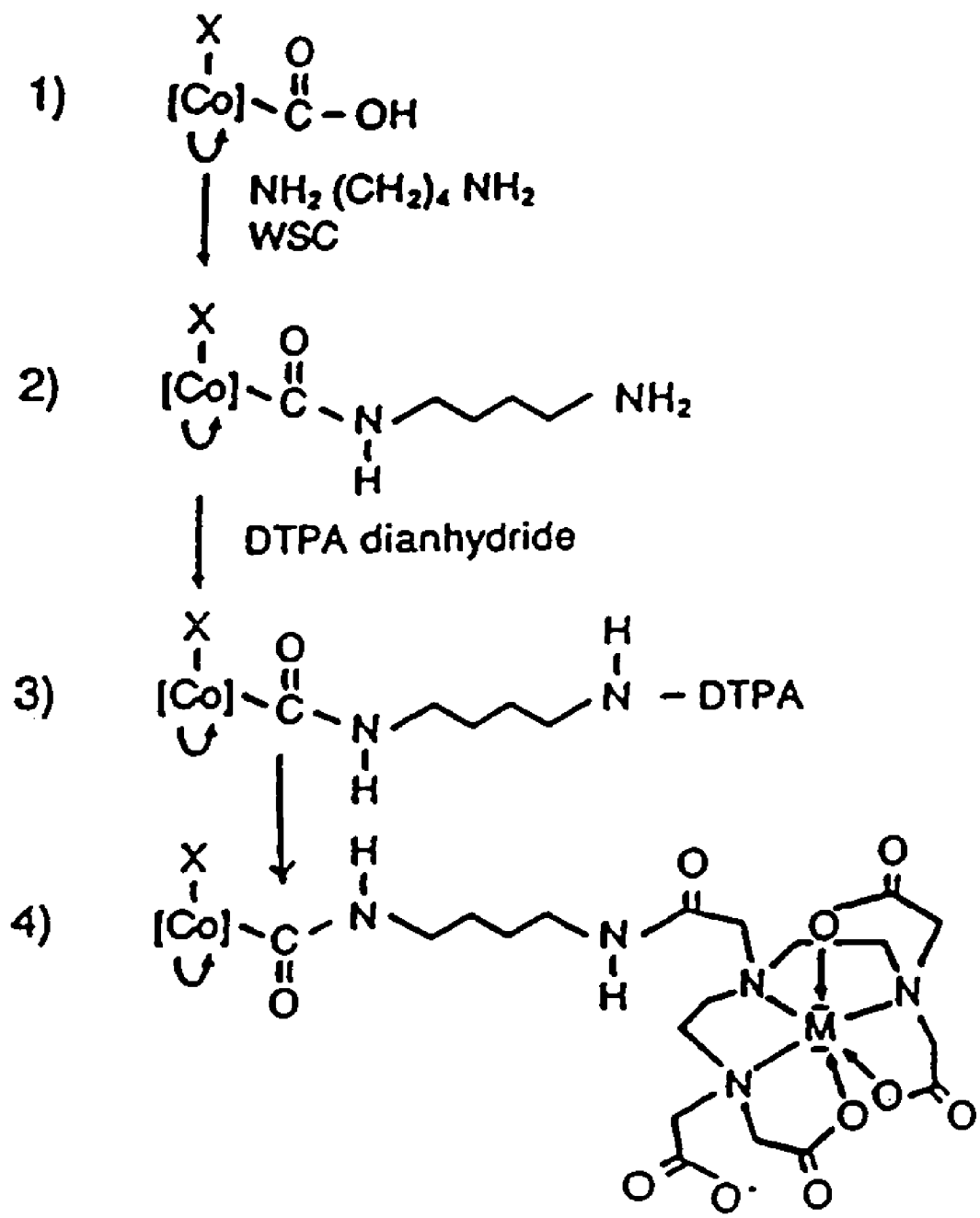
FIG. 2 schematically depicts the synthesis of a cobalamin metal ion DTPA complex.

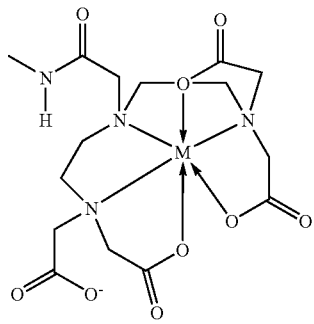

wherein M is the radionuclide. The synthetic route to a cobalamin metal ion DTPA complex (4) is schematically shown in FIG. 2, wherein WSC=water soluble carbodiimide.

The chelator (chel) DCTA has the general formula:

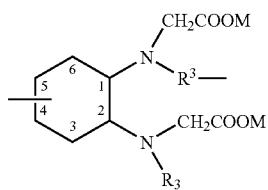

DCTA is a cyclohexane-based metal chelator, wherein $R^3$ may by $(C_1-C_4)$alkyl or $CH_2CO_2-$, which may be attached to the Y through positions 4 or 5, or through the group $R^3$ and which carries from 1 to 4 detectable metal or nonmetal cations (M), monovalent cations, or the alkaline earth metals. Thus, with metals of oxidation state +1, each individual cyclohexane-based molecule may carry up to 4 metal cations (where both $R^3$ groups are $CH_2COOM$). As is more likely, with higher oxidation states, the number of metals will decrease to 2 or even 1 per cyclohexane skeleton. This formula is not intended to limit the molecule to any specific stereochemistry. In particular, both amino functionalities may be either cis or trans to each other.

Other macrocyclic carboxylic acid chelators which can be linked to the cobalamin carboxylic acid via bis-amino linking groups include TETA 1,4,8,11-tetraazacyclotetradecane-N,N',N'',N'''-tetraacetic acid; 1,4,7,10-tetraazacyclododecane-N,N',N'',N'''-tetraacetic acid (DOTA); 1,4,8,12-tetraazacyclopentadecane-N,N',N'',N'''-tetraacetic acid (15N4); 1,4,7-triazacyclononane-N,N',N''-triacetic acid (9N3); and 1,5,9-triazacyclododecane-N,N',N''-triacetic acid (12N3). Bifunctional chelators based on macrocyclic ligands in which conjugation is via an activated arm attached to the carbon backbone of the ligand can be employed as described by M. Moi et al., *J. Amer. Chem. Soc.* 49, 2639 (1989) (2-p-nitrobenzyl-1,4,7,10-tetraazacyclododecane-N,N',N'',N'''-tetraacetic acid); S. V. Deshpande et al., *J. Nucl. Med.*, 31, 473 (1990); G. Ruser et al., *Bioconj. Chem.*, 1, 345 (1990); C. J. Broan et al., *J. C. S. Chem. Comm.*, 23, 1739 (1990); and C. J. Anderson et al., *J. Nucl. Med.* 36, 850 (1995) (6-bromoacetamido-benzyl-1,4,8,11-tetraazacyclotetadecane-N,N',N'',N'''-tetraacetic acid (BAT)).

Any metal capable of being detected in a diagnostic procedure in vivo or in vitro can be employed as M in the Det moieties. Particularly, any radioactive metal ion capable of producing a diagnostic result in a human or animal body or in an in vitro diagnostic assay may be used in the practice of the present invention. Suitable ions include the following: Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Cobalt-64, Erbium-169, Europium-152, Gadolinium-153, Gold-195, Gold-199, Hafnium-175, Hafnium-175–181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rubidium-86, Ruthenium-103, Ruthenium-106, Scandium44, Scandium46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium-95.

The compounds of formula (I) are preferable dissolved or dispersed in a nontoxic liquid vehicle, such as physiological saline or a similar aqueous vehicle, to the desired concentration. A preselected analytical, diagnostic or therapeutic unit dose is then administered to the test animal or human patient, by oral administration or ingestion or by parenteral administration, as by intravenous or intraperitoneal infusion or injection, to attain the desired in vivo concentration. Doses useful for imaging or treating human organs or tumors can be derived, from those found to be effective to image or treat organs in humans in vitro or in animal models, such as those described hereinbelow, or from dosages of other labelled vitamin $B_{12}$ molecules, previously employed in animal therapy or imaging.

The invention will be further described by reference to the following detailed examples, wherein cyanocobalamin and 1-ethyl-3-(3-dimethylaminopropyl) carbodiimide were purchased from Sigma Chem. Co., St. Louis, Mo. Adenosine, 1,4-diaminobutane dihydrochloride, diethylenetriamine pentaacetic (DPTA), hexamethylphosphoramide, 1-hydroxybenzotriazole hydrate, iodomethane and thionylchloride were obtained from Aldrich Chem. Co., Milwaukee, Wis. Thin layer chromatography (TLC) silica gel and PETellulose sheets were purchased from E. M. Science, Gibbstown, N.J. $Tc^{99m}$ and $In^{111}$ were obtained from Mallinckrodt Medical, Inc. and $Gd^{153}$ was obtained from Amersham. Other inorganic salts and solvents were obtained in the highest purity available.

UV-visible spectra were recorded on a Hewlett-Packard diode array spectrophotometer. DTPA dianhydride and 5'-chloro-5'-deoxyadenosine were synthesized as described by W. C. Eckelman et al., *J. Pharm. Sci.*, 64, 704 (1975) and K. Kikugawa et al., *Tetrahedron Lett.* 87 (1971), respectively. The monocarboxylic acids of cyanocobalamin, methylcobalamin-b-carboxylic acid and adenosylcobalamin-b-carboxylic acid were prepared and isolated as described by H. P. C. Hogenkamp, *Biochemistry*, 13, 2736 (1974); D. L. Anton et al., *J. Amer. Chem. Soc.* 102, 2215 (1980); R.H. Yamada et al., *J. Biol. Chem.*, 247, 6266 (1972) and D. Dolphin, *Methods in Enzymology*, XVille, 34–52 (1971).

Methylcobalamin, adenosylcobalamin and their derivatives are light sensitive, especially in solution, and all reactions and manipulations were carried out in the dark or in dim light.

All images for the in vivo studies were obtained on a GE 500 maxicamera using a LEAP collimator with a 20% window about the 140 keV energy peak of technetium, and a medium energy collimator with a 20% window about the 174 keV and 247 keV energy peaks of Indium. A 256×256 matrix with a dedicated pinnacle computer system was used to collect and analyze the data.

EXAMPLE 1

Cyanocobalamin-b-(4-aminobutyl)amide

A mixture containing cyanocobalamin-b-carboxylic acid (1.0 g, 0.6 mmol), hydroxybenzotriazole (0.81 g, 6 mmol) and 1,4-diaminobutane dihydrochloride (4.8 g, 30 mmol) in 100 ml of water was adjusted to pH 7.8. 1-Ethyl-3-(3'-dimethylaminopropyl)carbodiimide (1.26 g, 6.6 mmol) was then added, the pH was adjusted to 6.4 and the reaction stirred at room temperature for 24 h. TLC on silica gel using n-butanol-acetic acid water (5:2:3) showed the reaction to be complete. Cyanocobalamin-b-(4-aminobutyl)amide was extracted into 92% aqueous phenol and the phenol layer was washed several times with equal volumes of water. To the phenol extract were added 3 volumes of diethylether and 1 volume of acetone. The desired cobalamin was removed from the organic phase by several extractions with water. The combined aqueous layers were extracted three times with diethylether to remove residual phenol, concentrated to approximately 20 ml in vacuo and crystallized from aqueous acetone. Yield 955 mg, 92%.

EXAMPLE 2

Cyanocobalamin-b-(4-aminobutyl)amide DTPA

Cyanocobalamin-b-(4-aminobutyl) amide (500 mg), 0.3 mmol) was dissolved in 30 ml sat. sodium bicarbonate and treated with solid DTPA dianhydride (1.2 g, 3.4 mmol). The progress of the reaction was monitored by TLC on PEI plates using n-butanol-acetic acid-water (5:2:3) as the solvent. After 30 min incubation at room temperature a second 1.2 g of the dianhydride was added. After two additional additions of dianhydride with adjustments of the pH to 8.2 the reaction mixture was incubated overnight. Cyanocobalamin-DPTA adduct was then extracted into 92% aqueous phenol and purified as described above. The preparation was evaporated to dryness in vacuo and isolated as a glass. Yield 460 mg, 77%. The cyanobalamin-DTPA adduct behaves as a polyanion on paper electrophoresis in 0.1 M sodium phosphate buffer pH 7.1.

EXAMPLE 3

Methylcobalamin-b-(4-aminobutyl)amide

Methylcobalamin-b-carboxylic acid (1.0 g, 0.6 mmol) was reacted with diaminobutane dihydrochloride as described above for the cyano derivative. The cobalamin was purified by extraction through phenol (see above) and the resulting aqueous solution was concentrated in vacuo. This solution was chromatographed on AG1-X2 200–400 mesh in the acetate form (20×2.5 cm) and the pass through collected. The pass through was concentrated to approximately 20 ml and the desired cobalamin crystallized from aqueous acetone. Yield 920 mg, 88%. Unreacted methylcobalamin-b-carboxyclic acid was eluted with 1 M acetic acid, concentrated and crystallized from aqueous acetone. Yield 60 mg, 6%.

EXAMPLE 4

Methylcobalamin-b-(4-aminobutyl)amide DTPA

Methylcobalamin-b-(4-aminobutyl)amide (500 mg, 0.3 mmol) was dissolved in 30 ml saturated sodium bicarbonate and reacted with solid DTPA dianhydride as described above. The methyl cobalamin-DTPA adduct was purified by extraction through phenol, evaporated to dryness in vacuo and isolated as a glass. Yield 600 mg, 96%.

EXAMPLE 5

Adenosylcobalamin-b-(4-aminobutyl)amide

Adenosylcobalamin-b-carboxylic acid (500 mg, 0.3 mmol) was reacted with diaminobutane dihydrochloride (2.4 mg, 15 mmol) as described above. The cobalamin was purified by extraction through phenol (see above). The resulting aqueous solution was concentrated in vacuo and applied to AG-50 X2, 200–400 mesh, in the hydrogen form (20×25 cm). The column was washed thoroughly with water to remove hydroxybenzotriazole and the desired cobalamin eluted with 1 M ammonium hydroxide. After an additional extraction through phenol, adenosylcobalamin-b-(4-aminobutyl)amide was isolated as a glass. Yield 366 mg, 77%.

EXAMPLE 6

Adenosylcobalamin-b-(4-aminobutyl)amide DTPA

Adenosylcobalamin-b-(4-aminobutyl)amide (366 mg, 0.23 mmol) was dissolved in 30 ml saturated sodium bicarbonate and treated with solid DTPA dianhydride (1.0 g, 2.8 mmol) as described above. The cobalamin was purified through phenol (see above). The resulting aqueous solution was concentrated and applied to AG-50 X2, 200–400 mesh, in the hydrogen form (6.0×2.5 cm), the column was washed with water and the desired cobalamin eluted with 0.1 M ammonium hydroxide. The solution was evaporated to dryness in vacuo and adenosylcobalamin-b-(4-aminobutyl) amide DTPA isolated as a glass. Yield 400 mg, 80%.

EXAMPLE 7

Interaction with Intrinsic Factor and Transcobalamin Proteins

Under dim light, 1000 μg of the non-labeled methyl-, adenosyl-, and cyanocobalamin-b-(4-aminobutyl)amide-DTPA, as well as 1000 μg of cyanocobalamin and DTPA (Sigma, St. Louis, Mo. 63178), were separately dissolved in 10 ml of normal saline at room temperature. Each of the five 1000 μg/10 ml samples were stored in sealed, aluminum-wrapped 10 ml vials to prevent exposure to light. No buffers were added to the solutions. The pH of the solutions, measured by a Beckman 40 pH meter (Beckman Instruments, Fullerton, Calif.): Cyanocobalamin=5.75, DTPA=3.78; cyano, methyl and adenosylcobalamin-DTPA analogues were 5.75, 6.10, and 6.19, respectively.

To assess in vitro binding to Intrinsic Factor (IF) and Transcobalamins (TC), the intrinsic factor blocking antibody (IFBA) and Unsaturated vitamin $B_{12}$ Binding Capacity (UBBC) assays were performed with serum randomly obtained from five patients being evaluated for pernicious anemia at the Mayo Clinic. The IFBA and UBBC assays were first performed for clinical purposes as previously described by V. F. Fairbanks et al., *Mayo Clin. Proc.*, 58, 203 (1983); Intrinsic Factor Blocking Antibody [$^{57}$Co] Radioassay-Package insert, Diagnostic Products Corp.; D. Grossowicz et al., *Proc. Exp. Biol.*, 109, 604 (1962) and C. Gottlieb et al., *Blood* 25, 6 (1965).

Next, the serum from the same five patients underwent modified IFBA and UBBC assays. Specifically, 1 μl of the five previously described solutions were separately incubated with purified IF or serum, to potentially saturate all IF and TC binding sites. After incubation for 20 minutes at room temperature and for another 20 minutes at 4° C., 500 μl of the stock (1000 μg/l) Cobalt-57-cyanocobalamin (Mallinckrodt Medical. Inc., St. Louis, Mo. 63134) solution was added and the usual IFBA and UBBC protocols were then followed. All supernatant activity was counted for four minutes on a gamma counter (Micromedix 10/20, Huntsville, Ala. 35805). The results are shown in Table I.

solutions to IF was: cyanocobalamin=92.5%; methylcobalamin-b-(4-aminobutyl)-amide-DTPA=63.2%; cyanocobalamin-b-(4-aminobutyl)-amide-DTPA=52.9%; adenosylcobalamin-b-(4-aminobutyl)-amide-DTPA=41.0% and 0.8% for DTPA. This is in contrast to the disclosure in Houts (U.S. Pat. No. 4,465,775) that the (b)-monocarboxylic acid of vitamin $B_{12}$ and its radioiodinated derivative exhibit very low binding to IF.

Likewise the averaged percent binding of the five solutions to the transcobalamin proteins was: cyanocobalamin=100%, methylcobalamin-b-(4-aminobutyl)amide-DTPA=94.0%, adenosylcobalamin-b-(4-aminobutyl)amide-DTPA=90.4%, cyanocobalamin-b-(4-aminobutyl)amide-DTPA=66.4% and 3.6% for DTPA.

Thus, the attachment of DTPA to vitamin $B_{12}$ does alter its binding to the carrier proteins. As expected, non-labeled cyanocobalamin had the greatest affinity for IF and the transcobalamin proteins. Methylcobalamin-b-(4-aminobutyl)amide-DTPA was next, followed by adenosylcobalamin-b-(4-aminobutyl)amide-DTPA, and finally cyanocobalamin-b-(4-aminobutyl)amide-DTPA. There was also some nonspecific binding of DTPA to the carrier proteins (0.8% and 3.6%).

TABLE I

| Clinical Run | $CNB_{12}$ | $MEB_{12}DTPA$ | $ADB_{12}DTPA$ | $CNB_{12}DTPA$ | DTPA |
|---|---|---|---|---|---|
| UBBC | | | | | |
| PT 1 | 741 | <NSB | 17.1 | 54.6 | 222.6 | 731.5 |
| PT 2 | 632 | <NSB | 26.8 | 62.6 | 216.9 | 913.1 |
| PT 3 | 2097 | <NSB | 278.9 | 590.3 | 713.3 | 2078.9 |
| PT 4 | 1378 | <NSB | 60.9 | 126.9 | 433.2 | 1633.7 |
| PT 5 | 1682 | <NSB | 91.1 | 163.9 | 643.2 | 1418.0 |
| IFBA | | | | | |
| PT 1 | 11942.5 | 951.5 | 4279 | 6758.5 | 5151 | 11899 |
|  | (0.99) | (12.48) | (2.77) | (2.30) | (2.30) | (0.99) |
| PT 2 | 11656 | 920.5 | 4082 | 6841.5 | 5133.5 | 11696.5 |
|  | (1.02) | (12.90) | (2.92) | (1.74) | (2.31) | (1.02) |
| PT 3 | 11780 | 912.5 | 4456.5 | 6828.5 | 5338.5 | 11735.5 |
|  | (1.01) | (13.01) | (2.66) | (1.74) | (2.22) | (1.01) |
| PT 4 | 11617 | 749 | 4414 | 7046.5 | 6002.5 | 11909 |
|  | (1.02) | (15.85) | (2.69) | (1.64) | (1.98) | (1.00) |
| PT 5 | 11653.5 | 858.5 | 4381.5 | 7096.5 | 5973.5 | 11778.5 |
|  | (1.02) | (10.91) | (2.77) | (1.72) | (1.99) | (1.02) |

NSB = Nonspecific binding; counts < 100 consistent with saturation of transcobalamin proteins
Negative reference for IFBA; no binding to intrinsic factor (<1.11)
Positive reference for IFBA; binding to intrinsic factor (>1.43)
Indeterminate reference value (1.11 → 1.43)
Clinical Run = patients supernatant counts from UBBC and IFBA assays
DTPA = diethylenetriamine pentaacetic acid
$CNB_{12}$ = cyanocobalamin
$MEB_{12}$ DTPA = methylcobalamin-b-(4-aminobutyl)-amide-DTPA
$ADB_{12}$ DTPA = adenosylcobalamin-b-(4-aminobutyl)-amide-DTPA
$CNB_{12}$ DTPA = cyanocobalamin-b-(4-aminobutyl)-amide-DTPA The IFBA assay demonstrated that DTPA does not significantly bind to IF (values less than the negative reference), whereas cyanocobalamin and the cobalamin-DTPA analogs do, in varying degrees, competitively inhibit Co-57 cyanocobalamin from binding to intrinsic factor. By using the counts of the Clinical run divided into the counts of the five solutions, the efficacy of binding to intrinsic factor can be estimated. The averaged percent binding of the five

EXAMPLE 8

Chelation of Radionuclides.

Under dim light, 1000 μg of methyl-, adenosyl-, and cyanocobalamin-b-(4-aminobutyl)amide-DTPA were separately dissolved in 200 μl of normal saline. Next, 500 μCi of Indium-111 or 250 μCi of Gadolinium-153 were added to the cobalamin-DTPA solutions. The reactions were carried out at room temperature and room air. For the chelation of technetium, the dissolved cobalamin DTPA complexes were separately placed into sealed 2 ml vials. Next, 200 µl of stannous chloride solution (1000 µg/ml normal saline) were added to each vial. The vials were purged with nitrogen gas for 5 minutes. After this time, 1–5 mCi of Technetium-99m was added to the $N_2$ purged vials. Each vial underwent further nitrogen purging for 5 minutes. All chelation reactions were mixed gently for 5 minutes.

Control mixtures of 1000 µg of cyanocobalamin were dissolved in 200 µl of normal saline. Cyanocobalamin was mixed with Tc-99m at room temperature and room air, as well as within nitrogen purged vials containing 200 µl of the described stannous chloride solution. Additionally, the cobalamin-DTPA complexes underwent Tc-99m labeling in open vials at room air in the absence of the stannous chloride.

Specific activity was assessed by mixing 100 µl aliquots of methyl and adenosyl cobalamin-b-(4-aminobutyl)amide-DTPA (5 µg/100 µl normal saline) with 50 µl stannous chloride solution (1 µg/50 µl normal saline) in nitrogen purged 2 ml vials. Technetium-99m in 10, 25, 50, 75, and 100 mCi allotments of activity were added to the vials. The vials underwent gentle mixing and continuous nitrogen purging for five minutes after the addition of technetium.

Efficiency of chelation and specific activity were assessed via thin layer chromatography (TLC). Thin layer chromatographic strips (Grade 31 ET Chr-thickness 0.50 mm, flow rate (water) 225 mm/30 min, Whatman Lab Sales, Hilsboro, Oreg. 97123) were developed in acetone in dim light. The dry strips were placed on film (Ektascan-MC1, Eastern Kodak. Rochester, N.Y. 14650) for autoradiography (AR). Chromatographic and autoradiographic results were visually compared. All the radiolabeled cobalamin-DTPA complexes underwent TLC and AR to confirm 100% labeling prior to in vivo administration.

Under acetone development, free Tc-99m migrates to the top of the chromatographic strip, whereas In-111 and Gd-153 diffusely spread over the lower two-thirds of the strip. TLC and AR analysis demonstrated that there was 100% labeling of all three cobalamin-DTPA complexes with Tc-99m, In-111, and Gd-153. Specifically, all radioactivity was confined to the chromatographic distribution of the cobalamin analogues.

Since methyl and adenosyl cobalamin could potentially have greater uptake in malignant tissue, the chelation of Tc-99m, In-111, and Gd-153 by methyl and adenosylcobalamin-b-(4-aminobutyl)amide-DTPA underwent greater scrutiny. The chromatographic and autoradiographic images were consistently coincident. In contrast, unmodified cyanocobalamin did not demonstrate any affinity for binding the three radionuclides. As expected, there was minimal labeling of the cobalamin-DTPA complexes with Tc-99m in the absence of stannous chloride and hypoxic conditions.

At a concentration of 5 µg/100 µl the red color of the cobalamin-DTPA analogues is barely discernible in the aqueous state, and undetectable on TLC. However, the AR distribution is the same when compared to the more concentrated cobalamin analogue solutions with lower specific activity. Methyl and adenosyl cobalamin-b-(4-aminobutyl) amide-DTPA can chelate up to 50 mCi of technetium-99m per 5 µg with 100% efficiency. This results in a specific activity of 10 mCi/µg for the cobalamin-DTPA analogue.

EXAMPLE 9

In Vivo Studies

A. Biodistribution: Methylcobalamin-b-(4-aminobutyl) amide-DTPA in a concentration of 300 µg/100 µl normal saline was labeled with 3 mCi of Indium-111. The labeled vitamin $B_{12}$ analogue was diluted Keith normal saline to a final volume of 1000 µl. Via intraperitoneal injection (IP), five 12 week old female Balb-C mice (Harlan, Sprague, Dawley, Indianapolis, Ind. 46229) each received 200 µl (500 µCi) of the methylcobalamin-DTPA-$^{111}$In complex. For comparison, Indium-111-DTPA having the same concentration and specific activity of the methylcobalamin-DTPA analogue, was injected IP into three mice. All mice were sacrificed at 24 hours via $CO_2$ inhalation. The pancreas, spleen, kidneys, and heart were dissected in their entirety. A portion of the liver, lung, left quadricep muscle, and flank fat were also harvested. All tissue samples and organs were weighed wet minced in 2.0 ml normal saline, and counted for five minutes in a gamma well counter (Minaxi Autogamma 5000, Packard Instrument, Downers Grove, Ill. 60515).

B. Gastrointestinal Absorption: Methylcobalamin-b-(4-aminobutyl)-DTPA and DTPA alone were labeled as described above, with the exception that the 3 mCi Indium/300 µg/100 µl normal saline solutions were not diluted. Two groups of three mice had a few drops of either $^{111}$In-DTPA or methylcobalamin-b-(4-aminobutyl)-DTPA-111In placed in their oral cavities. The mice were sacrificed at 24 hrs, dissected, and studied as described above.

A modified Schillings test was performed on two mice. Specifically, each mouse received via subcutaneous and intraperitoneal administration, a 1000 µg loading dose of non-labeled methylcobalamin-b-(4-aminobutyl)amide-DTPA analogue. At 24 hrs, the mice were fed 2–3 drops of Indium-labeled methylcobalamin-b-(4-aminobutyl)amide-DTPA-complex. Urine and feces were collected from the three groups of mice after oral administration. The mice were sacrificed at 24 hours after ingestion of tracer and images and biodistribution data were obtained at that time.

C. Tumor Imaging: At 24 hours, there was a significant amount of adenosylcobalamin-b-(4-aminobutyl) amide-DTPA-In-111 uptake within the transplanted sarcoma both visually and by gamma well counting (Table II).

TABLE II

|  | Kidney | Liver | Spleen | Pancreas | Heart | Lung | Fat | Muscle | Tumor |
| --- | --- | --- | --- | --- | --- | --- | --- | --- | --- |
| Mouse 1 | 3717.5 | 943.3 | 433.1 | 304.2 | 134.7 | 130.9 | 101.4 | 93.6 | — |
| Mouse 2 | 3299.5 | 823.4 | 405.3 | 319.9 | 189.4 | 180.1 | 147.3 | 51.4 | — |
| Mouse 3 | 3462.7 | 768.6 | 366.8 | 310.3 | 171.2 | 113.1 | 102.8 | 43.9 | — |
| Mouse 4 | 224.0 | 56.9 | 44.1 | 13.4 | 10.3 | 6.2 | 12.6 | 5.4 | — |
| Mouse 5 | 130.2 | 41.5 | 26.2 | 13.0 | 6.9 | 6.0 | 19.5 | 5.6 | — |
| Mouse 6 | 281.6 | 66.1 | 57.7 | 14.1 | 12.5 | 10.5 | 18.8 | 5.0 | — |
| Mouse 7 | 621.4 | 126.4 | 67.8 | 40.0 | 35.0 | 38.4 | — | 13.6 | — |

TABLE II-continued

|          | Kidney | Liver | Spleen | Pancreas | Heart | Lung  | Fat   | Muscle | Tumor  |
|----------|--------|-------|--------|----------|-------|-------|-------|--------|--------|
| Mouse 8  | 700.5  | 111.7 | 66.6   | 39.3     | 29.8  | 51.2  | —     | 12.4   | —      |
| Mouse 9  | 601.7  | 115.8 | 66.3   | 41.2     | 31.3  | 40.6  | —     | 12.0   | —      |
| Mouse 10 | 119.4  | 24.0  | 19.5   | 6.0      | 5.6   | 5.4   | —     | 8.9    | —      |
| Mouse 11 | 117.3  | 25.5  | 19.0   | 6.7      | 5.0   | 5.3   | —     | 2.6    | —      |
| Mouse 12 | 110.1  | 23.2  | 18.1   | 5.9      | 4.8   | 5.0   | —     | 3.7    | —      |
| Mouse 13 | 4.3    | 0.82  | 0.67   | 0.75     | 0.54  | 1.1   | <BKG  | <BKG   | —      |
| Mouse 14 | 4.1    | 0.80  | 0.70   | 0.76     | 0.54  | 0.33  | <BKG  | <BKG   | —      |
| Mouse 15 | 3.1    | 0.73  | 0.65   | 1.1      | 0.50  | 0.44  | <BKG  | <BKG   | —      |
| Mouse 16 | 0.64   | 0.28  | 0.62   | 0.93     | <BKG  | <BKG  | <BKG  | <BKG   | —      |
| Mouse 17 | 0.54   | 0.21  | 0.67   | 0.96     | <BKG  | <BKG  | <BKG  | <BKG   | —      |
| Mouse 18 | 0.59   | 0.30  | 0.48   | 0.61     | <BKG  | <BKG  | <BKG  | <BKG   | —      |
| Mouse 19 | 3886.9 | 691.0 | 576.3  | 445.0    | 165.0 | 318.8 | 76.0  | 70.1   | 954.7  |
| Mouse 20 | 3115.6 | 464.8 | 309.5  | 242.7    | 134.8 | 230.0 | 170.4 | 81.9   | 1426.0 |
| Mouse 21 | 3592.8 | 675.0 | 478.3  | 439.0    | 157.8 | 335.2 | 198.0 | 166.5  | 1183.1 |
| Mouse 22 | 116.5  | 19.7  | 17.3   | 7.1      | 5.0   | 4.5   | 13.7  | 7.2    | 52.8   |
| Mouse 23 | 180.7  | 40.9  | 22.6   | 11.3     | 8.0   | 9.2   | 17.9  | 6.4    | 69.3   |
| Mouse 24 | 231.2  | 60.3  | 46.1   | 13.9     | 9.7   | 8.5   | 19.2  | 6.8    | 73.1   |
| Mouse 25 | 543.9  | 116.5 | 54.7   | 38.4     | 21.7  | 34.4  | 39.5  | 23.5   | 135.5  |
| Mouse 26 | 240.8  | 56.2  | 25.8   | 21.3     | 11.4  | 19.9  | 13.5  | 15.5   | 60.4   |
| Mouse 27 | 459.2  | 107.6 | 37.1   | 30.3     | 16.9  | 21.3  | 17.8  | 14.5   | 120.3  |
| Mouse 28 | 14.0   | 1.6   | 1.9    | 1.4      | 0.94  | 1.7   | 0.93  | .68    | 5.0    |
| Mouse 29 | 9.9    | 1.3   | 1.4    | 8.2      | 0.61  | 0.87  | 0.75  | .60    | 2.8    |
| Mouse 30 | 10.2   | 1.4   | 1.6    | 3.1      | 0.85  | 0.93  | 0.79  | .63    | 3.4    |

Mice 1–3 and 19–21 = 500 µCi adenosylcobalamin-b-(4-aminobutyl)-amide-DTPA-$^{111}$In injected intraperitoneal
Mice 4–6 and 22–24 = 500 µCi DTPA-$^{111}$In injected intraperitoneal
Mice 7–9 = 500 µCi adenosylcobalamin-b-(4-aminobutyl)-amide-DTPA-$^{111}$In injected subcutaneously
Mice 10–12 = 500 µCi DTPA-$^{111}$In injected subcutaneously
Mice 13–15 = approximately 30 µCi methylcobalamin-b-(4-aminobutyl)-amide-DTPA-$^{111}$In administered orally
Mice 16–18 = approximately 30 µCi DTPA-$^{111}$In administered orally
Mice 25–27 = approximately 100 µCi methylcobalamin-b-(4-aminobutyl)-amide-DTPA-$^{111}$In tailvein injection
Mice 28–30 = approximately 100 µCi DTPA-$^{111}$In tailvein injection Despite the difference in the amount of activity injected between IP and IV routes, the degree of uptake within the tumor was consistently second behind the kidneys. The tumors had two to four times greater activity than the liver, spleen, and pancreas, with 4–12 times greater activity than that of the heart, lungs, fat, and muscle. As expected, no activity was seen to localize in the left flank of the control mice. Usual uptake in the liver and spleen was again seen. Gross pathology of the dissected masses demonstrated fat encapsulated tumors. Microscopically, by H & E stain, the tumors were solid masses of blue stained cells consistent with a sarcoma No areas of necrosis were noted.

Although DTPA-$^{111}$In demonstrated uptake within the transplanted tumors, its concentration was 10–20 times less than that of adenosylcobalamin-DTPA-$^{111}$In.

D. Intravenous Administration: One milligram of either methyl or adenosylcobalamin-b-(4-aminobutyl)amide-DTPA was labeled with 5 mCi of $^{99m}$Tc as described above. Several mice were sacrificed via $CO_2$ inhalation at varying time intervals after tailvein injection. The first urine passed was collected and analyzed via TLC and AR.

E. Results

1. In Vivo Studies (a) Biodistribution

The organ and tissue distribution of the methyl and adenosylcobalamin-DTPA analogs at 24 hours was similar despite the route of administration (Table II). The kidneys were first followed by the liver and spleen. The pancreas usually was next followed by the lungs, fat, heart, and muscle. The differences in activity between the pancreas, heart, lung, fat, and muscle was less significant after oral, subcutaneous, and intravenous administration. However, the ratio of uptake between the kidneys to liver, liver to spleen, and spleen to pancreas was relatively constant. The route of administration (IV, IP, PO) did not have any obvious effect on the chelation of Tc-99m or In-111 by these complexes.

The greatest amount of DTPA-$^{111}$In uptake was in the kidneys. The distribution of DTPA was similar to the cobalamin analogs, especially after intraperitoneal injection. Despite their similarities, DTPA-$^{111}$In had 5–12 times less activity per organ or tissue sample when compared to the methyl and adenosylcobalamin analogs.

(b) Gastrointestinal Absorption

Methylcobalamin-b-(4-aminobutyl) amide-DTPA-In-111 was absorbed from the gastrointestinal tract after oral administration. The majority of activity was localized in the kidneys, liver, and spleen on delayed imaging. In the mice that were not "flushed" with oral and intraperitoneal doses of non-labeled methylcobalamin-b-(4-aminobutyl) amide-DTPA, no discernable activity was detected in the urine by gamma well counting. However, the mice that underwent the "modified Schillings test" had detectable radioactivity within their urine at one hour. Imaging at 24 hours of these "flushed" mice demonstrated significantly less activity throughout the body when compared to the "non-flushed" mice. Fecal radioactivity became detectable at 2 hours in both groups receiving the radioactive cobalamin analogs orally.

DTPA-$^{111}$In was also absorbed from the gastrointestinal tract, but to a lesser degree. No activity was detected in the heart, lungs, muscle, or fat tissue samples. Radioactivity was detected in urine and stool by two hours.

(c) Intravenous Administration

Micturition occurred at approximately 15 and 45 minutes after intravenous and intraperitoneal injections, respectively. The first passed urine after intravenous or intraperitoneal administration was always radioactive. TLC and AR analysis of the collected urine showed no evidence of dissociation of the Tc-99m or In-111 from the cobalamin-DTPA complexes. Images at 5 minutes and 4 hours after tailvein injection demonstrated focal early uptake in the kidneys which became obscured by the liver and spleen activity on the delayed images.

(d) Tumor Imaging

At 24 hours, there was a significant amount of adenosylcobalamin-b-(4-aminobutyl) amide-DTPA-In-111 uptake within the transplanted sarcoma both visually and by gamma well counting (Table II). Despite the difference in the amount of activity injected between IP and IV routes, the degree of uptake within the tumor was consistently second behind the kidneys. The tumors had two to four times greater activity than the liver, spleen, and pancreas, with 4–12 times greater activity than that of the heart, lungs, fat, and muscle. As expected, no activity was seen to localize in the left flank of the control mice. Usual uptake in the liver and spleen was again seen. Gross pathology of the dissected masses demonstrated fat encapsulated tumors. Microscopically, by H & E stain, the tumors were solid masses of blue stained cells consistent with a sarcoma. No areas of necrosis were noted.

Although DTPA-$^{111}$In demonstrated uptake within the transplanted tumors, its concentration was 10–20 times less than that of adenosylcobalamin-DTPA-$^{111}$In.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of imaging or treating a tumor in a mammal comprising:
   administering an effective amount of a compound of formula (I) to said mammal:

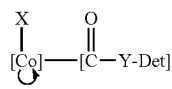
(I)

wherein the moiety

is cobalamin,

is the residue of a monocarboxylic acid of cobalamin, X is CN, OH, methyl or adenosyl, Y is a linking group and Det is a detectable chelating group comprising a radionuclide or a paramagnetic metal ion; and optionally detecting the compound of formula I in a tumor of the mammal.

2. The method of claim 1 wherein the radionuclide is a metallic radioisotope.

3. The method of claim 2 wherein the metallic radioisotope is Tc$^{99}$, In$^{111}$ or Gd$^{153}$.

4. The method of claim 1 wherein

is the residue of the (b)-monocarboxylic acid.

5. The method of claim 4 wherein Y is a divalent monomer, dimer or trimer of $N(H)(CH_2)_{2-6}N(H)$.

6. The method of claim 5 wherein Y is $-N(H)(CH_2)_4NH-$.

7. The method of claim 1 wherein Det is EDTA, DTPA, DOTA, TETA, or DCTA.

8. The method of claim 3 wherein Det comprises DTPA.

9. The method of claim 1, comprising administering to said mammal a detectable amount of the compound of in combination with a pharmaceutically acceptable vehicle, and detecting the presence of said compound in a tumor of the kidney, liver, pancreas, spleen, or intestine of said mammal.

10. The method of claim 9 wherein the administration is parenteral.

11. The method of claim 10 wherein the administration is intravenous.

12. The method of claim 11 wherein the administration is intraperitoneal.

13. The method of claim 9 wherein the administration is oral.

14. The method of claim 1 wherein the administration is parenteral.

15. The method of claim 1 wherein the administration is oral.

16. The method of claim 9 wherein the vehicle is an aqueous vehicle.

17. The method of claim 2 wherein the tumor is a liver, kidney, splenic, pancreatic, or gastrointestinal tumor.

18. The method of claim 2 wherein the metallic radioisotope is selected from the group consisting of Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Cobalt-64, Erbium-169, Europium-152, Gadolinium-153, Gold-195, Gold-199, Hafnium-175, Hafnium-175–181, Indium-111, Iridium-192, Iron55, Iron-59, Krypton-85, Lead-210, Manganese-54, Mercury-197, Mercury-203, Molybdenum-99, Neodymium-147, Neptunium-237, Nickel-63, Niobiumo-95, Osmium-185+191, Palladium-103, Platinum-195m, Praseodymium-143, Promethium-147, Protactinium-233, Radium-226, Rhenium-186, Rubidium-86, Ruthenium103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium-95.

19. The method of claim 1 wherein Det comprises a chelating group selected from the group consisting of EDTA, DTPA, DOTA, TETA, DCTA, 15N4, 12N3, 2-p-nitrobenzyl-1,4,7,10-tetraazacyclododecane-N,N',N'',N'''-tetraacetic acid, and BAT.

* * * * *